United States Patent
Bertram, III

(10) Patent No.: US 8,852,191 B2
(45) Date of Patent: Oct. 7, 2014

(54) CUTTING GUIDE AND METHOD FOR PERFORMING LATERAL RETINACULAR RELEASE

(75) Inventor: Morton Bertram, III, Naples, FL (US)

(73) Assignee: SurgenCo, LLC, Gulf Breeze, FL (US)

( * ) Notice: Subject to any disclaimer, the term of this patent is extended or adjusted under 35 U.S.C. 154(b) by 94 days.

(21) Appl. No.: 13/528,277

(22) Filed: Jun. 20, 2012

(65) Prior Publication Data

US 2012/0323245 A1    Dec. 20, 2012

Related U.S. Application Data

(60) Provisional application No. 61/498,728, filed on Jun. 20, 2011.

(51) Int. Cl.
*A61B 17/00* (2006.01)
*A61B 17/32* (2006.01)

(52) U.S. Cl.
CPC . *A61B 17/320016* (2013.01); *A61B 17/320036* (2013.01)
USPC ............................ 606/83; 606/102; 606/88

(58) Field of Classification Search
USPC .......... 606/79, 82–85, 176; 30/143, 481, 373, 30/162, 105, 90.4, 335
See application file for complete search history.

(56) References Cited

U.S. PATENT DOCUMENTS

| | | | |
|---|---|---|---|
| 5,269,796 A | | 12/1993 | Miller et al. |
| 5,470,335 A | * | 11/1995 | Du Toit ......................... 606/329 |
| 6,391,028 B1 | | 5/2002 | Fanton et al. |
| 6,685,717 B1 | | 2/2004 | Ilic |
| 8,486,077 B1 | * | 7/2013 | Kornel ......................... 606/86 R |
| 2009/0048620 A1 | | 2/2009 | Weiss et al. |
| 2010/0228083 A1 | | 9/2010 | Mirza et al. |
| 2010/0234848 A1 | * | 9/2010 | Sutterlin et al. ................ 606/79 |

FOREIGN PATENT DOCUMENTS

WO    WO-97/09936    3/1997

* cited by examiner

*Primary Examiner* — Andrew Yang
(74) *Attorney, Agent, or Firm* — Gifford, Krass, Sprinkle, Anderson & Citkowski, P.C.

(57) ABSTRACT

Apparatus and methods are used for severing at least a portion of a lateral retinaculum as part of a lateral release procedure. An elongated guide body has a first, smooth side and second, opposing side having a lengthwise track with a groove. A pushrod having a cutting device is insertable into the track such that the cutting device protrudes from the lengthwise groove, thereby enabling a user to move the pushrod and sever a lateral retinaculum using the cutting device. The cutting device may be a sharp blade or an electrocautery. A method of performing a lateral retinacular release may comprise the steps of inserting the elongated guide body under the skin and subcutaneous fat with the second, opposing side facing a lateral retinaculum; inserting the pushrod into the track of the body; and pushing or pulling the pushrod such that the cutting device severs a lateral retinaculum.

2 Claims, 3 Drawing Sheets

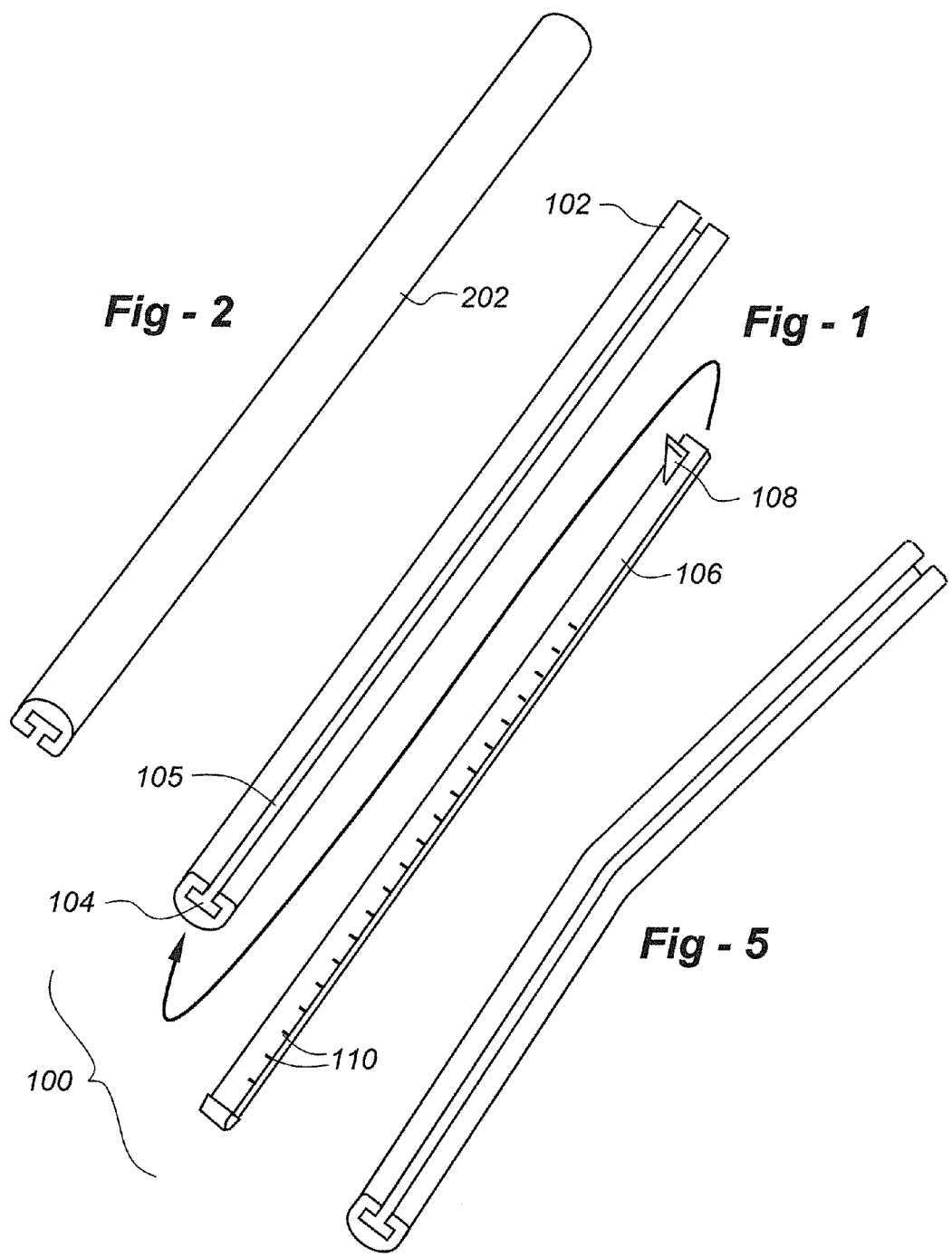

CUTTING GUIDE AND METHOD FOR PERFORMING LATERAL RETINACULAR RELEASE

REFERENCE TO RELATED APPLICATION

This application claims priority from U.S. Provisional Patent Application Ser. No. 61/498,728, filed Jun. 20, 2011, the entire content of which is incorporated herein by reference.

FIELD OF THE INVENTION

This invention relates generally to orthopedic surgery and, in particular, to apparatus and methods for performing a percutaneous, minimally invasive, lateral retinacular release procedure.

BACKGROUND OF THE INVENTION

A lateral release is a surgical procedure used to release tight capsular structures (lateral retinaculum) on the outer aspect (lateral aspect) of the kneecap (patella). The procedure is also known as a "lateral retinacular release." This is usually performed because of knee pain related to the patella being pulled over to the lateral side of the knee, such that the patella is not able to move properly in the center of the groove of the femur bone as the knee bends and straightens. In the human body, the lateral retinaculum and other soft tissues including the skin are only a few millimeters apart. Thus, one of the challenges of the procedure is to sever the lateral retinaculum while leaving the skin and surrounding tissues intact.

SUMMARY OF THE INVENTION

This invention resides in apparatus and methods for severing at least a portion of a lateral retinaculum as part of a lateral release procedure. The instrumentation comprises an elongated guide body having a first, smooth side and second, opposing side having a lengthwise track with a groove. A pushrod having a cutting device is insertable into the track such that the cutting device protrudes from the lengthwise groove, thereby enabling a user to move the pushrod and sever a lateral retinaculum using the cutting device.

The cutting device may be a sharp blade or an electrocautery device that protrudes from the groove. The elongated guide body may be bent, malleable or bendable. The guide may be on the order of 5-15 cm in length, more preferably in the range of 7.5 to 10 cm. The width of the guide may be on the order of 2-10 mm, more preferably in the range of 5 to 7.5 mm. The width of the groove 105 may be 1 mm or thereabouts. The length of the pushrod may be at least 6 cm, more preferably over 10 cm to allow a proximal grasping section during use. The blade may protrude from the guide by 2-10 mm, more preferably 3-7 mm, most preferably 5 mm. The end of the guide may be closed off so the cutting edge never leaves the track portion. The pushrod may include marking 110 to provide a depth reading.

A method of performing a lateral retinacular release comprising the steps of providing an elongated guide body having a first, smooth side and second, opposing side having a lengthwise track with a groove, and a pushrod having a cutting device is insertable into the track such that the cutting device protrudes from the lengthwise groove. The method continues by inserting the elongated guide body under the skin and subcutaneous fat with the second, opposing side facing a lateral retinaculum; inserting the pushrod into the track of the body; and pushing or pulling the pushrod such that the cutting device severs a lateral retinaculum.

BRIEF DESCRIPTION OF THE DRAWINGS

FIG. 1 is a drawing that shows the preferred embodiment of the invention;

FIG. 2 is a drawing that shows the smooth, backside of the device of FIG. 1;

FIG. 5 shows a bent guide according to the invention to accommodate the patellar mound, if desired.

DETAILED DESCRIPTION OF THE INVENTION

Figure 3:
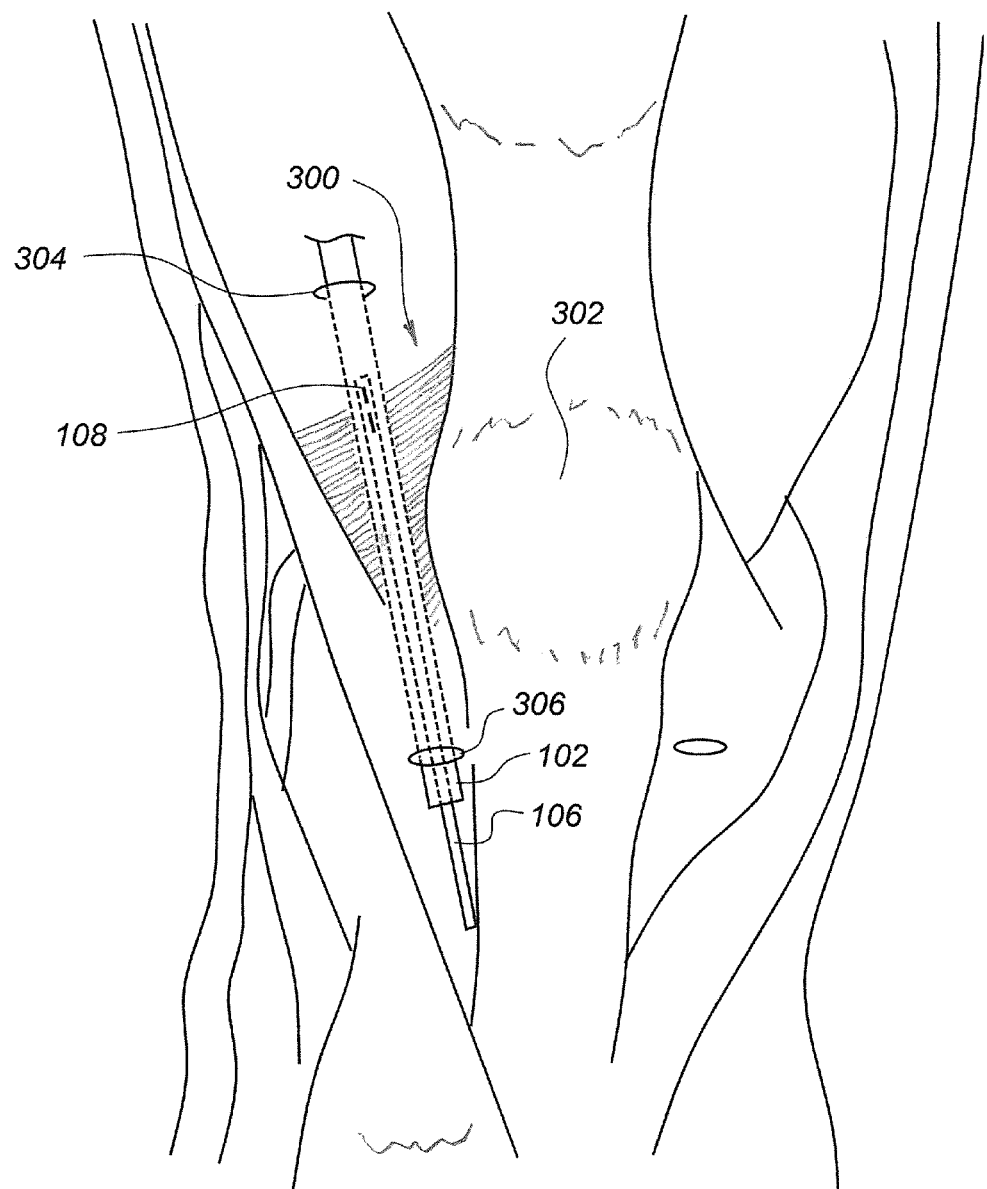
FIG. 3 is a drawing that illustrates a lateral retinacular release procedure utilizing the invention.

This invention provides a cutting guide and methods that facilitate a controlled severing of the lateral retinaculum while protecting surrounding tissues.

FIG. 1 is a drawing that shows the preferred embodiment of the invention generally at 100. The system includes a guide 102 having a track 104 and a pushrod 106 having a cutting blade 108. The track is shown as T-shaped, with the pushrod 106 having a generally rectangular cross section such that during movement the blade 108 protrudes out the elongate groove 104 from track 104. FIG. 2 illustrates the backside of the guide, showing a smooth outer surface 202. It will be appreciated that other track and pushrod dimensions are possible to long as controlled movement of the blade is achieved.

In terms of dimensions, the guide 102 is on the order of 5-15 cm in length, more preferably in the range of 7.5 to 10 cm. The width of the guide is on the order of 2-10 mm, more preferably in the range of 5 to 7.5 mm. The width of the groove 105 is 1 mm or thereabouts. The length of the pushrod is at least 6 cm, more preferably over 10 cm to allow a proximal grasping section during use. The blade 108 preferably protrudes from the guide by 2-10 mm, more preferably 3-7 mm, most preferably 5 mm. The end of the guide may be closed off so the cutting edge never leaves the track portion. The pushrod may include marking 110 to provide a depth reading.

Although the blade 108 is shown to provide a forward cutting motion, the cutting edge may be located on the proximal edge to facilitate cutting while pulling on the pushrod 106. The blade 108 may have cutting edges on both sides enabling cutting in both forward and reverse directions. The blade may be spring biased or mechanically operated with a guide wire such that the blade is retracted to prevent or minimize cutting then flipped out to facilitate cutting. The cutting blade may be replaced or augmented with an electrocautery device, in which case two electrodes would protrude from the slot 105 as opposed to a cutting blade.

The guide may be constructed of metal or plastic, and may be disposable in either case. The guide may be provided in a bent shape as shown in FIG. 5 to course around the patellar mound, if desired. The bend may be on the order of 5-35 degrees, more preferably 20 degrees or thereabouts. As opposed to being provided in a bent shape, the guide 102 may be provided as a formable or malleable material enabling the surgeon to bend the guide in accordance with patient anatomy. The pushrod may likewise be constructed of metal or plastic, preferably plastic if a bent guide or electrocautery cutter is used.

Figure 4:
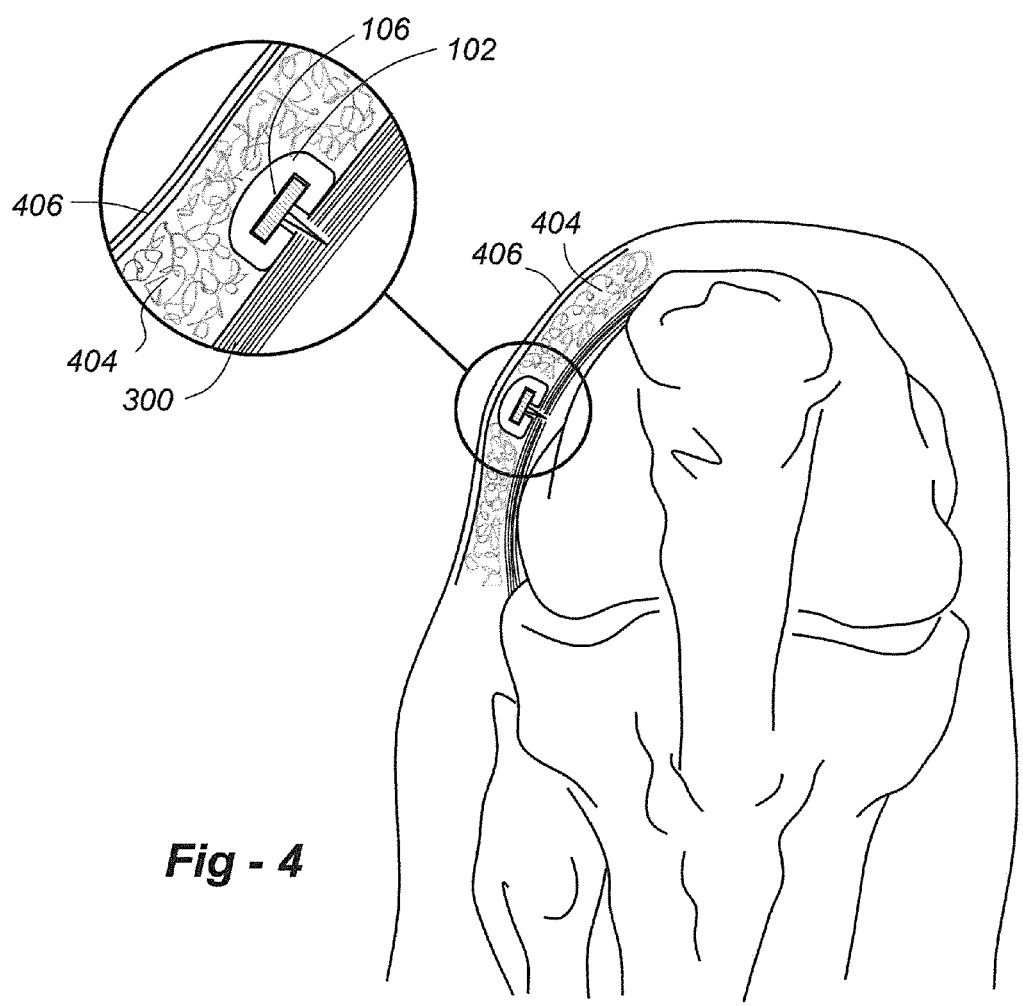
FIG. 4 is an anterior view of the knee in flexion showing the disposition of the guide during a release procedure.

FIG. 3 is a drawing that illustrates a release procedure utilizing the invention. The lateral retinaculum is depicted at 300, with the patella being shown at 302. FIG. 4 is an anterior view of the knee in flexion showing the disposition of the guide during the procedure. The guide 102 is tunneled under the skin 406 and subcutaneous fat 404 laterally from a small incision superiorly 304 to the arthroscope portal 306 inferiorly the zipper. The smooth side 202 faces the fat and skin layers and the track side faces the lateral retinaculum. Once the guide body is in place, the pushrod is inserted inferiorly into the track 104. The blade 108 straddles the lateral retinaculum and severs it as it is pushed superiorly cutting the tissue as it is pushed.

As shown in FIG. 3, the guide body 202 made have a bend such as 20 degrees to form to patient anatomy. Particularly if electrocautery is used as opposed to a knife edge, the guide may be made of disposable plastic as opposed to metal.

The invention claimed is:

1. Surgical instrumentation for severing the lateral retinaculum with respect to a lateral release procedure, comprising:
    an elongated guide body having a lengthwise inner track with proximal and distal ends, a first, smooth lengthwise surface and a second, opposing surface with a lengthwise groove into the lengthwise track;
    a pushrod with proximal and distal ends, with the distal end of the pushrod having a single cutting device operative to sever biological tissue, the pushrod being insertable into the track such that the single cutting device protrudes from the lengthwise groove and the second, opposing surface, thereby enabling a user to move the pushrod and sever a lateral retinaculum using the single, protruding cutting device; and
    wherein pushrod includes depth markings.

2. A method of performing a lateral retinacular release, comprising the steps of:
    providing an elongated guide body having a lengthwise inner track with proximal and distal ends, a first, smooth lengthwise surface and a second, opposing surface with a lengthwise groove into the lengthwise track, and a pushrod with proximal and distal ends, with the distal end of the pushrod having a single cutting device operative to sever biological tissue, the pushrod being insertable into the track such that the single cutting device protrudes from the lengthwise groove and the second, opposing surface, thereby enabling a user to move the pushrod and sever a lateral retinaculum using the single, protruding cutting device;
    inserting the elongated guide body under the skin and subcutaneous fat with the second, opposing side facing a lateral retinaculum;
    inserting the pushrod into the track of the body; and
    pushing or pulling the pushrod such that the cutting device severs a lateral retinaculum.

* * * * *